United States Patent [19]

Bombart

[11] Patent Number: 5,292,532
[45] Date of Patent: Mar. 8, 1994

[54] AQUEOUS ANTIFUNGAL VAGINAL DOUCHE

[76] Inventor: Felice Bombart, 240 East 27th Street, Apt. 6J, New York, N.Y. 10016

[21] Appl. No.: 958,609

[22] Filed: Oct. 8, 1992

Related U.S. Application Data

[63] Continuation of Ser. No. 752,161, Aug. 21, 1991, abandoned, and a continuation of Ser. No. 633,224, Dec. 21, 1990, abandoned.

[51] Int. Cl.$^5$ ............... A01N 25/04; A01N 43/16; A01N 43/52
[52] U.S. Cl. ................... 424/405; 424/430; 424/433
[58] Field of Search ............ 424/422, 426, 430, 434, 424/405, 433

[56] References Cited

U.S. PATENT DOCUMENTS 4,895,727  1/1990  Allen ................................ 424/642
5,043,155  8/1991  Puchalski et al. .................... 424/78
5,158,774  10/1992  Inman ................................ 424/430

OTHER PUBLICATIONS

Remingtons Pharmaceutical Sciences, Mack Publishing Co. (1988) Edition.

*Primary Examiner*—Thurman K. Page
*Assistant Examiner*—Neil Guy
*Attorney, Agent, or Firm*—Rochelle K. Seide

[57] ABSTRACT

An aqueous vaginal douche which is at most marginally effective against bacteria but which includes a fungicidal/fungistatic agent to rid the vaginal zone of yeasts. The douche may include a penetrating agent and/or an adherent to hold the fungicidal/fungistatic agent to the vaginal tissues. The douche is inserted into the vagina by means of a nozzle or the like. The douche may incorporate a carrier or solvent for the fungicidal/fungistatic agent and may further include a preservative.

13 Claims, No Drawings

AQUEOUS ANTIFUNGAL VAGINAL DOUCHE

This is a continuation of copending application Ser. No. 07/752,161 filed on Aug. 21, 1991, abandoned, which in turn, is a continuation, of application Ser. No. 633,224, filed Dec. 21, 1990 now abandoned.

FIELD OF INVENTION

This invention relates to vaginal douches and more particularly to vaginal douches incorporating therein fungicidal/fungistatic (fungicidal and/or fungistatic) agents. This invention also relates to methods for preparing and utilizing vaginal douches which include fungicidal/fungistatic agents.

BACKGROUND

There are three types of compositions available that can be hygienically administered to the vaginal zone. The simplest is essentially water acting as a cleansing agent. A second type contains povidone-iodine. This product is effective against bacteria, but not against fungi. The presence of normal bacterial flora in the vagina is desirable, should not be reduced, and does not cause discomfort. The presence of fungal overgrowth in the vagina is undesirable causing discomfort and infection. Therefore, povidone-iodine is considered to be unsuitable for preferred hygienic administration to the vaginal area.

A third type of treatment consists of pharmaceutically acceptable fungicidal/fungistatic compositions which are effective. However, the methods of application for these products are cumbersome and insufficiently effective. The products that are supplied in tablet form require insertion into the vagina with the aid of a mechanical device. The tablet thereafter disintegrates and is distributed throughout the vagina to come in contact with the fungi in order to be effective. This method of treatment is not very effective. Miconazole nitrate supplied in a cream formulation is also cumbersome to apply vaginally and the difficulty of thorough distribution to all tissue surfaces reduces its effectiveness.

In reviewing prior art patents, relative to the preparation of this application there were uncovered U.S. Pat. Nos. 3,011,946 (Bartner et al); 4, 195, 172 (Falkowski et al) and 4,102,998 (Gutnick).

The Bartner patent develops an aqueous solution of nystatin which is highly soluble in an aqueous solution of a soluble saccharin. The discovery discloses that the incorporation of benzyl alcohol into the solution imparts an improved solubility to the nystatin. According to the patentee, nystatin preparations are parenterally administered and administration is intended to be by injection in an intramuscular or intravenous fashion. This is different from the administration of a vaginal douche by means of a nozzle or the like.

The Falkowski patent relates to salts of various compounds including nystatin which are of very high water solubility. The resulting compounds are said to exhibit antifungal activity. This patent relates to injectable solutions and not to the administration of douches. One of the specified nystatin salts derived is N-methylglucamine salt of the N-glycosyl derivative of nystatin.

The Gutnick patent relates to a process for the prevention of venereal disease. It embodies a metal intrauterine contraceptive device for medication, which is released gradually into the vagina and the lower end of the uterus over a prolonged period of time. This patent relates to antibacterials and antibiotics and the device includes a magnet. Reference is also made to antifungal activity in other places in the text of this patent, but nystatin is referred to as an antibiotic with antifungal activity. No reference is made to a water soluble nystatin.

None of the known prior art nor the forgoing patents relates to the preparation of a fluid douche especially suited for killing or inhibiting fungi such as yeast in the vaginal zone while being at most marginally effective with respect to bacteria.

SUMMARY OF INVENTION

It is an object of the invention to provide an improved vaginal douche.

It is another object of the invention to provide an improved vaginal douche capable of eradicating or minimizing the presence of fungi.

It is still another object of the invention to provide an improved aqueous vaginal douche capable of eradicating fungi while being at most marginally effective relative to bacteria of the type normally found in the vaginal zone.

It is still another object of the invention to provide an improved vaginal douche and methods for the use thereof based on recognition of the facts that, 1) it is harmful to remove the bacteria from the vaginal zone and 2) that it is of substantial importance to eradicate fungi such as yeast in the vaginal zone.

In achieving the above and other objects of the invention, there is provided a method comprising effecting hygienic cake of a vaginal zone by introducing into the vaginal zone a fluid douche into which has been incorporated a fungicidal/fungistatic agent. More particularly the fungicidal/fungistatic agent which is employed in accordance with the invention has at most a marginal effectiveness against bacteria especially of the type normally found in the vaginal zone.

As features of the invention, the method thereof further comprises enhancing the penetration of the douche into the vaginal zone by incorporating into the douche a penetrating agent. According to a further feature of the invention there is comprised in the method thereof the enhancing of adhering of the fungicidal/fungistatic agent to the tissue in the vaginal zone by incorporating into the douche an adherent adapted to retain the fungicidal/fungistatic agent in the vaginal zone.

Preferably in accordance with the invention the fluid douche is prepared with water as the fluid whereby to form an aqueous douche. Preferably the adherent is a gum such as for example selected from the group consisting of arabic, align, guar, tragacanth, pectin, dextran and xanthan. The aforesaid gums are natural gums. A further group which is useful in providing an adherent in accordance with the invention is a modified natural gum. These may be selected from the group consisting of sodium carboxymethyl cellulose, methyl cellulose, hydroxyethyl cellulose, hydroxypropyl cellulose, and hydroxyethyl methyl cellulose. The gum employed in accordance with the invention may also be a synthetic gum such as polyvinyl alcohol, polyacrylic acid and polyvinyl pyrrolidine. Acidic gums may be used as is or as their salts, for example, formulated with sodium or potassium hydroxide, or organic amines such as triethanol amine, monoisopropanol amine or di-(2-ethyl hexyl) amine.

The penetrant which is employed may be a nonionic agent selected from a group consisting of ethoxylated alcohols, ethoxylated alkyl phenols, ethoxylated fatty acids, ethoxylated castor oil, alkanolamides, ethylene glycol/propylene glycol copolymers, ethoxylated sorbitol, ethoxylated sorbitol esters and ethoxylated glycerol esters. The penetrant may also be an anionic agent selected from a group consisting of alkyl sulfosuccinates, alkyl sulfonates and sulfates, alkyl aryl sulfonates and sulfates, phosphate esters and betaines.

In accordance with the invention the fungicidal/fungistatic agent may be of various types. Some examples which are employed in accordance with the invention include miconazole, 1-[2-(2,4-dichlorophenyl)-2-[(2,4-dichlorophenyl) methoxy]ethyl]-1H-imidazole; clotrimazole, 1-[(2-chlorophenyl)diphenylmethyl)-1H-imidazole; ketoconazole, cis-1-acetyl-4-[4-[[2-(2,4-dichlorophenyl)-2-(1H-imidazol-l-ylmethyl)-1,3-dioxolan-4-yl]-methoxy]phenyl]piperazine; and nystatin.

According to the invention the dispersion and solution of the fungicidal/fungistatic agent in water may be enhanced by incorporating a carrier or solvent into the douche. The carrier may be for example polyethylene glycol or polypropylene glycol and preferably one having a molecular weight range from about 200–2000.

Preferably the douche will be adjusted to a pH of about 5.5 to 8.5. In addition there may be incorporated a preservative in the douche such as for example methylparaben or propylparaben. The douche of the invention is introduced into the vaginal zone via a nozzle inserted therein.

This invention also relates to the provision of a product. This product comprises a vaginal douche including a fungicidal/fungistatic agent having at most a marginal effectiveness against bacteria. The vaginal douche in accordance with the invention is an aqueous douche. Preferably the aqueous douche includes a penetrating agent and/or an adherent of the above noted type.

The above and other objects, features, and advantages will become apparent from the following detailed description of some preferred embodiments thereof.

DETAILED DESCRIPTION

The purpose of this product is to provide prompt hygienic direct relief from vaginal itch and irritation caused by fungal overgrowth and fungal types of infection. This preparation is in the form of a douche for easily administered direct refreshing application, providing thorough distribution, adherance and penetration of the vaginal zone.

Vaginal itch and irritation secondary to fungal overgrowth is a very common problem plaguing approximately 50% of the female population. This type of vaginitis is caused by fungal overgrowth.

A mild amount of fungal overgrowth will cause persistent itch, irritation, and foul smelling discharge. A substantial amount of fungal overgrowth causes unbearable constant itching, severe inflammation and profuse foul smelling discharge, therefore an enormous amount of discomfort. Fungal infections are communicable.

In normal amounts, vaginal bacteria keeps in check or limits fungal overgrowth. A decrease in the amount of normal vaginal bacterial flora will allow fungal overgrowth.

Altered and/or decreased vaginal bacterial flora is caused by 1) antibiotic therapy, 2) chemotherapy, 3) altered immunologic conditions such as AIDS, and De George Syndrome, 4) cancer, 5) stress and 6) poor nutrition. Fungal overgrowth is also caused by altered metabolic states such as diabetes mellitus. For those females with diabetes mellitus, fungal overgrowth in the vagina is a chronic problem and requires constant treatment throughout one's lifetime. A significant amount of healthyll females also have chronic yeast overgrowth of unknown etiology.

Presently on the market there is no douche that can treat or decrease fungal overgrowth in the vagina. On the contrary, aqueous products or douches used in the vagina can cause a decrease in normal bacterial flora, altering the normal balance between bacteria and fungi, thereby promoting fungal overgrowth.

There is also on the market a douche containing a povidone-iodine solution which is bactericidal, thereby decreasing the amount of bacteria and directly promoting fungal overgrowth.

In prescription form there exists treatments with pharmaceutically acceptable fungicidal/fungistatic compositions. However, the method of application for these products is cumbersome and insufficiently effective. The products are supplied in tablet and cream form and require insertion into the vagina with the aid of a mechanical device. The tablet by itself must then disintegrate and distribute throughout the vagina to come in contact with the fungi in order to be effective. This method of treatment is ineffective. Miconazole nitrate supplied in a cream formulation is also cumbersome to apply vaginally using a mechanical device and the difficulty of thorough distribution to all tissue surfaces reduces its effectiveness.

The invention overcomes the above deficiencies by providing an uncombersome, refreshing, effective product in a form that is easy to use. The product is formulated to be rapidly distributed throughout the vagina and vaginal zone for purposes of reaching all tissue surfaces. Ingredients are, in accordance with the invention, included in the composition to enhance penetration, and adherence, to-the tissue surfaces in the vaginal zone.

Pharmaceutically acceptable fungicidal/fungistatic agents for the product include miconazole, 1-[2-(2,4-dichlorphenyl)-2-[(2,4-dichlorophenyl) methoxy]ethyl]-1H-imidazole; clotrimazole, 1-[(2-chlorophenyl) diphenylmethyl)-1-Himidazole; ketoconazole, cis-i-acetyl-4-[4[[2-(2,4-dichlorophenyl)-2-(1H-imidazol-1-ylmethyl)-1,3-dioxolan-4-yl]-methoxy]phenyl]piperazine; and nystatin. These substances are known for their fungicidal/fungistatic properties. The first three are synthetic substances; the last, nystatin, is a polyene antibiotic obtained from a microorganism culture. Their effectiveness against bacteria is marginal and, therefore, they will not disturb the normal bacterial balance in the vagina.

The composition of the invention is enhanced by incorporating a gum to provide adherence to the vaginal tissues. Natural gums may be used such as arabic, align, guar, tragacanth, pectin, dextran, and xanthan. Modified natural (semisynthetic) gums may be used such as sodium carboxymethyl cellulose, methyl cellulose, hydroxyethyl cellulose, hydroxypropyl cellulose and hydroxyethyl methyl cellulose. Synthetic gums such as polyvinyl alcohol, polyacrylic acid and polyvinyl pyrrolidine may also be used. Acidic gums may be used as is, or as their salts. For example, these gums can be formulated with sodium or potassium hydroxide, or organic amines such as triethanol amine, monoisopropanol amine or di-(2-ethyl hexyl) amine.

A penetrant is incorporated to hasten and improve the penetration and adherence of the fungicide to the tissue surfaces. Nonionic penetrants may be used such as ethoxylated alcohols, ethoxylated alkyl phenols, ethoxylated fatty acids, ethoxylated castor oil, alkanolamides, ethylene glycol/propylene glycol copolymers, ethoxylated sorbitol, ethoxylated sorbitol esters and ethoxylated glycerol esters. Anionic penetrants may also be used such as alkyl sulfosuccinates, alkyl sulfonates and sulfates, alkyl aryl sulfonates and sulfates, phosphate esters and betaines.

The compositions also contain a carrier or solvent for the components to assist in the dispersion and solution of the ingredients in water for efficient introduction and distribution within the vagina. No mechanical device is required as with the use of a fungicide in tablet or cream form. Suitable carriers are polyethylene glycols (PEG), also known as polyoxyethylene glycols (POE), and polypropylene glycols (PPG), also known as polyoxypropylene glycols (POP). Grades in the molecular weight range 200-2000 are suitable. A 400 molecular weight grade is preferred.

Minor percentages (for example, up to about 1%) of other components may be included in the following examples to render the compositions more pharmaceutically desirable. The pH may be adjusted to 5.5-8.5 as desired with tactic acid, citric acid, their sodium salts, or similar substances. Preservatives may be added as desired, such as methylparaben, propylparaben or similar substances. Suitable fragrances may be added as desired.

| EXAMPLE 1 | |
|---|---|
| | Wt % |
| Miconazole | 1-3 |
| Tragacanth | 1-3 |
| *Nonyl phenol polyethylene glycol | 1-3 |
| Polyethylene glycol 400 | 97-91 |
| | 100 |

*Tergitol NP-10 (Union Carbide Corp) containing 10.5 mols of ethylene oxide.

All ingredients are mixed at 20-50 degrees Celsius producing a solution or dispersion in the glycol. 4-5 parts of the product are mixed with 100-150 parts of water producing a concentration of 0.025-0.15% clotrimazole for vaginal treatment. Insertion into the vaginal zone is by means of a nozzle or the like.

The following Examples 2-6 are prepared it the same manner as that used for Example 1.

| | Wt % |
|---|---|
| EXAMPLE 2 | |
| Clotrimazole | 1-3 |
| *Polyacrylic acid | 1-3 |
| Triethanol amine | 1-3 |
| **Ethoxylated castor oil | 1-3 |
| Polyethylene glycol 400 | 96-88 |
| | 100 |
| EXAMPLE 3 | |
| Ketoconazole | 1-3 |
| Pectin | 1-3 |
| Nonyl phenol polyethylene glycol | 1-3 |
| Polyethylene glycol 400 | 97-91 |
| | 100 |
| EXAMPLE 4 | |
| Nystatin | 1-3 |
| Dextran | 1-3 |
| Ethoxylated castor oil | 10-30 |
| Polyethylene glycol 400 | 88-64 |
| | 100 |

-continued

| | | Wt % |
|---|---|---|
| EXAMPLE 5 | | |
| Clotrimazole | | 1-3 |
| Ethoxylated castor oil | | 10-30 |
| Polyethylene glycol 400 | | 89-67 |
| | | 100 |
| EXAMPLE 6 | | |
| Clotrimazole | | 1-3 |
| Polyacrylic acid | | 1-3 |
| Triethanol amine | | 1-3 |
| Polyethylene glycol 400 | | 97-91 |
| | | 100 |
| ***EXAMPLE 7 | | |
| (A) | Clotrimazole | 1-3 |
| | Polyethylene glycol 400 | 99-97 |
| | | 100 |
| (B) | Algin | 1-5 |
| | Nonyl phenol polyethylene glycol | .01-.5 |
| | Water | 98.99-94.5 |
| | | 100 |
| ****EXAMPLE 8 | | |
| (A) | Clotrimazole | 1-3 |
| | Ethoxylated castor oil | 99-97 |
| | | 100 |
| (B) | Arabic | 1-5 |
| | Water | 99-95 |
| | | 100 |
| ##EXAMPLE 9 | | |
| Clotrimazole | | .03-.2 |
| Polyacrylic acid | | .03-.2 |
| Triethanol amine | | .03-.2 |
| Ethoxylated castor oil | | 3-20 |
| Water | | 96.91-79.4 |
| | | 100 |
| ****EXAMPLE 10 | | |
| (A) | Clotrimazole | 1-3 |
| | Ethoxylated castor oil | 99-97 |
| | | 100 |
| (B) | Polyacrylic acid | .03-.2 |
| | Triethanol amine | .03-.2 |
| | Water | 99.94-99.6 |
| | | 100 |

*Carbopol 934; Goodrich Chemical Co.
**POE (40) Castor oil; Trylox CO-40, Code 5909; Henkel Corp., Emery Group.
***(A) is prepared by mixin the ingredients at 20-5 degrees Celsius. 4-5 parts of (A) are added and mixed with 100-150 parts of (B) at ambient temperature and used immediately as a vaginal douche.
All ingredients are mixed at 20-50 degrees Celsius.
****Prepared and used as Example 7.

There will now be obvious to those skilled in the art many modifications and variations of the method and products set forth above. These modifications and variation will not depart from the scope of the invention defined by the following claims.

What is claimed is:

1. An aqueous antifungal vaginal douche composition consisting essentially of an antifungal agent selected from the group consisting fomiconazole, clotrimazole, ketoconazole and nystatiin in an amount effective to kill and/or inhibit the growth of yeasts or fungi in the vagina, a penetrating agent selected from the group consisting of ethoxylated alcohols, ethoxylated alkylphenols, ethoxylated fatty acids, ethoxylated castor oil, alkanolamides, ethylene glycol/propylene glycol copolymers, ethoxylated sorbitol, ethoxylated sorbitol esters, ethoxylated glycerol esters, alkyl sulfosuccinates, alkyl sulfonates, alkyl sulfates, alkyl aryl sulfonates, alkyl aryl sulfates, phosphate esters and betaines in an amount effective to enhance penetration of the antifungal agent into vaginal tissue, an adherent agent selected from the group consisting of arabic, align, guar, tragacanth and xanthan gums, pectin, dextran, sodium carboxymethyl cellulose, methyl cellulose, hydroxyethyl cellulose, hydroxypropyl cellulose, hydroxyethyl methyl cellulose, polyvinyl alcohol, polyacrylic acid and acidic gums in an amount effective to enhance adherence of the antifungal agent to vaginal tissue and a carrier or solvent selected from the group consisting of polyethylene glycols, polyoxyethylene glycols, polypropylene glycols and polyoxypropylene glycols, wherein said douche composition has a pH of about 5.5. to 8.5 and will not disturb the normal bacterial balance in the vagina.

2. The douche composition of claim 1 wherein the antifungal agent is miconazole.

3. The douche composition of claim 1 wherein the antifungal agent is clotrimazole.

4. The douche composition of claim 1 wherein the antifungal agent is ketoconazole.

5. The douche composition of claim 1 wherein the antifungal agent is nystatin.

6. The douche composition of claim 1 wherein the effective amount of antifungal agent is between 0.03-3.0 weight percent of the composition.

7. The douche composition of claim 1 wherein the penetrating agent is a nonionic agent selected from the group consisting of ethoxylated alcohols, ethoxylated allyl phenols, ethoxylated fatty acids, ethoxylated castor oil, alkanolamides, ethylene glycol/propylene glycol copolymers, ethoxylated sorbitol, ethoxylated sorbitol esters and ethoxylated glycerol users.

8. The douche composition of claim 1 wherein the penetrating agent is an anionic agent selected from the group consisting of lakyl sulfo succinates, alkyl sulfonates, alkyl sulfates, alkyl aryl sufonates, alkyl aryl sulfates, phosphate esters and betaines.

9. The douche composition of claim 1 wherein the adherent agent is a natural gum selected from the group consisting of arabic, align, guar, tragacanth and xanthan gums, pectin and dextran. pH of about 5.5. to 8.5 and will not disturb the normal bacterial balance in the vagina.

10. The douche composition of claim 1 wherein the adherent agent is a modified natural gum selected from the group consisting of sodium carboxy methycellulose, methyl cellulose, hydroxyethyl cellulose, hydroxypropyl cellulose, and hydroxyethyl methyl cellulose.

11. The douche composition of claim 1 wherein the adherent agent is a synthetic gum selected from the group consisting of polyvinyl alcohol and polyacrylic acid.

12. The douche composition of claim 1 wherein the carrier has a molecular weight between 200-2000.

13. The douche composition of claim 12 wherein the carrier has a molecular weight of 400.

* * * * *